United States Patent [19]

Noack

[11] Patent Number: 5,080,251

[45] Date of Patent: Jan. 14, 1992

[54] TORTUOUS PATH IN-PATIENT ROOM MEDICAL WASTE DISPOSAL CONTAINER

[75] Inventor: William L. Noack, Camarillo, Calif.

[73] Assignee: Devon Industries, Inc., Chatsworth, Calif.

[21] Appl. No.: 595,748

[22] Filed: Oct. 4, 1990

Related U.S. Application Data

[63] Continuation of Ser. No. 387,347, Jul. 28, 1989, abandoned.

[51] Int. Cl.⁵ .............................................. B65D 83/10
[52] U.S. Cl. ..................... 220/335; 220/254; 220/910; 220/259; 232/47; 206/366
[58] Field of Search ............... 220/908, 910, 254, 256, 220/259, 334, 335; 206/365, 366; 232/43.1, 43.2, 44, 47, 57

[56] References Cited

U.S. PATENT DOCUMENTS

| | | | |
|---|---|---|---|
| 86,698 | 2/1869 | Sawyer | 220/908 |
| 253,519 | 2/1882 | Drew | 220/259 |
| 508,325 | 11/1893 | Lewis | 220/908 |
| 524,637 | 8/1894 | Johnson | 232/47 |
| 613,795 | 11/1898 | Costello | 232/47 |
| 618,624 | 1/1899 | Stanek et al. | 220/334 |
| 4,874,103 | 10/1989 | Quisenberry et al. | 220/254 |
| 4,917,263 | 4/1990 | Korb | 220/908 |
| 4,953,732 | 9/1990 | Cocks | 220/908 |
| 4,955,477 | 9/1990 | Bruno | 206/366 |
| 4,969,554 | 11/1990 | Sawaya | 206/366 |

Primary Examiner—Stephen Marcus
Assistant Examiner—S. Castellano
Attorney, Agent, or Firm—Poms, Smith, Lande & Rose

[57] ABSTRACT

A medical instrument disposal container has a hollow bin member fitted with a hollow top housing member, the two members having mating flanges with snap lock means for holding them together, the hollow top member further having a rectangular medical instruments entry port which may be closed by a closure lid which has a snap lock type locking means which engages with portions of the top member to affect a substantially permanent closure of the port. Internally of the hollow top housing member, and below the entry port, there is provided a tortuous path means including first and second oppositely inclined barrier walls which block manual entry into the interior of the hollow bin member but allow for the free fall introduction of medical instruments, syringes, sharps, or other medical materials into the storage area of the bin member. In a preferred embodiment, one of the barrier walls may pivot upwardly toward the entry port by the force of gravity when the container is inverted to prevent the accidental discharge of the container contents.

10 Claims, 5 Drawing Sheets

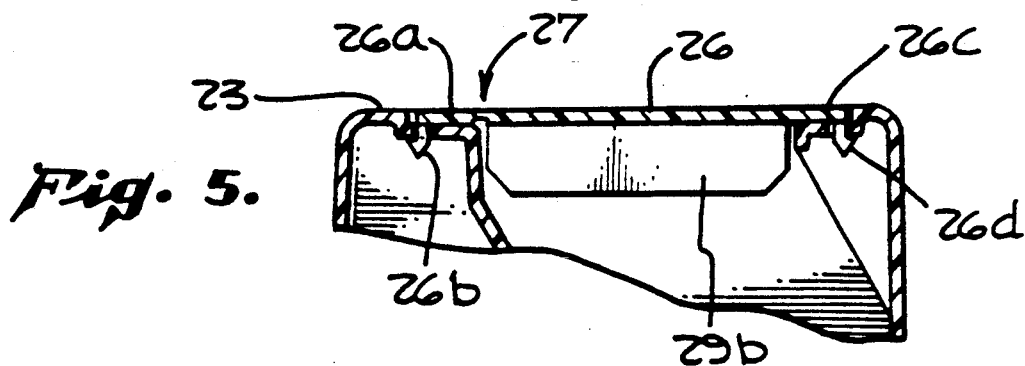
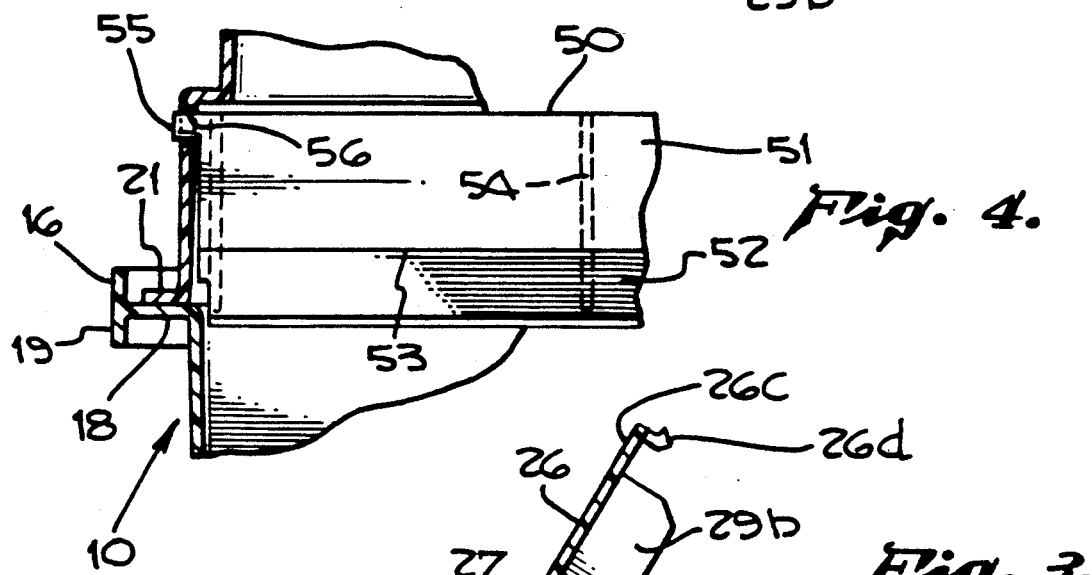
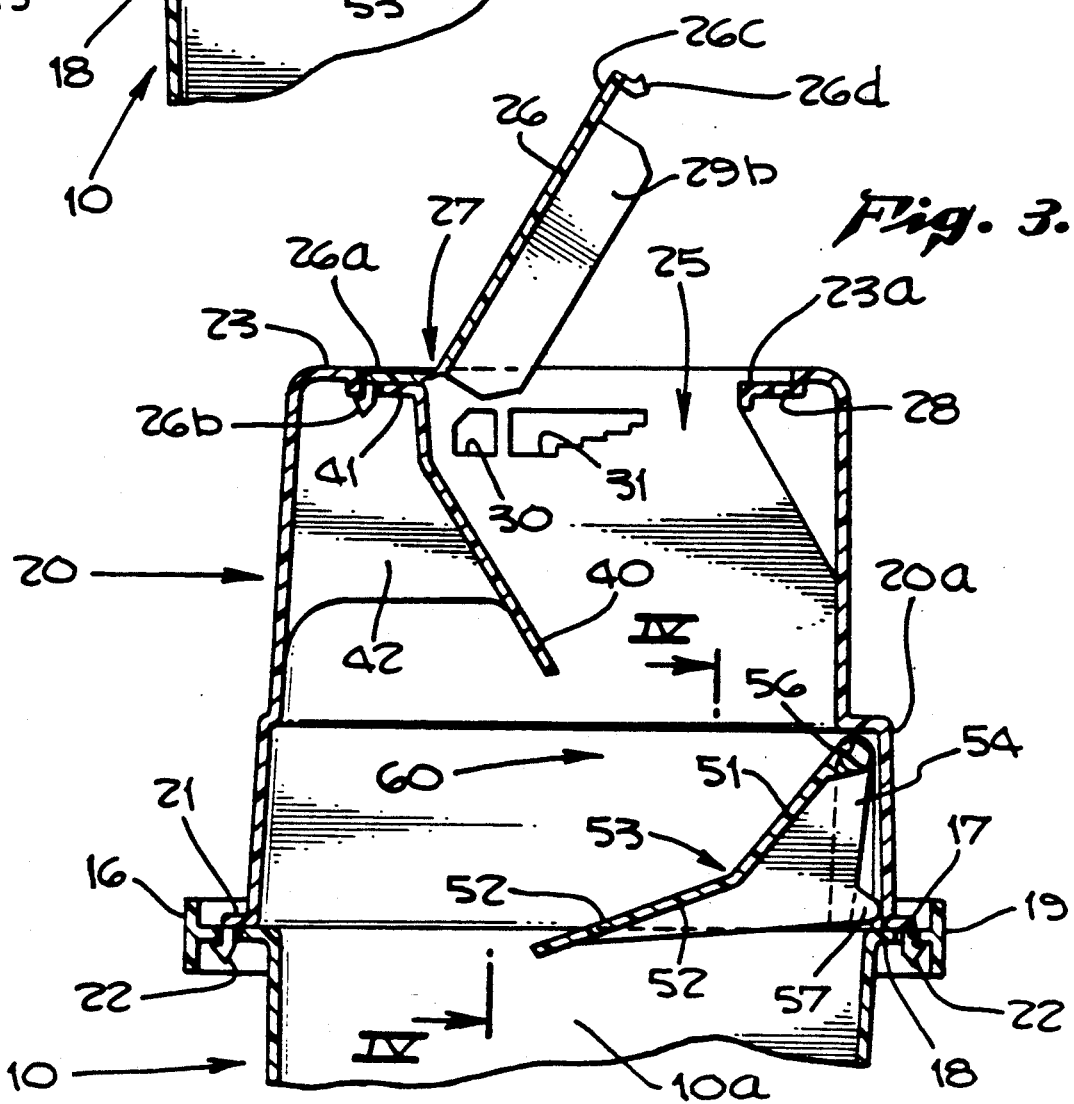

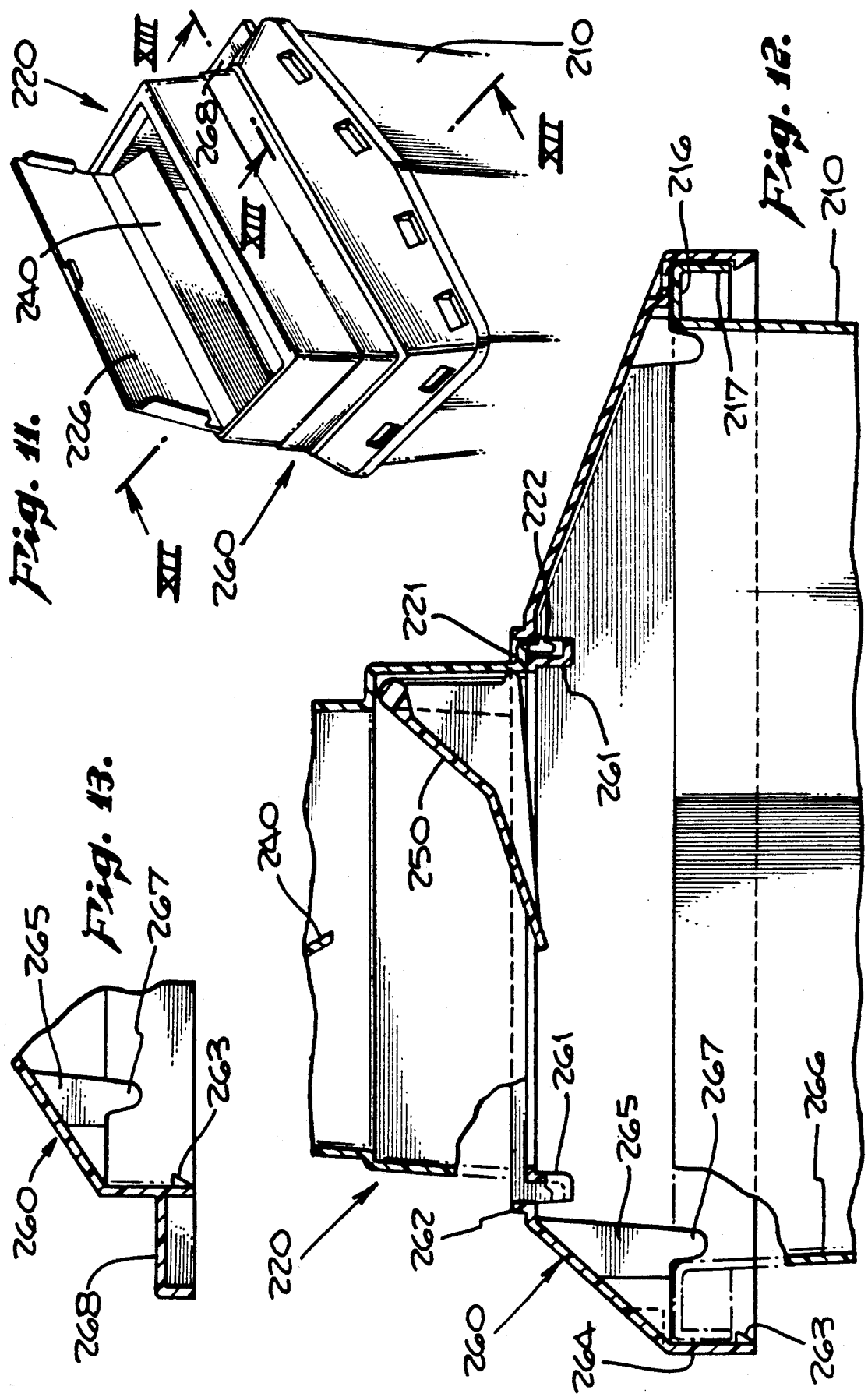

TORTUOUS PATH IN-PATIENT ROOM MEDICAL WASTE DISPOSAL CONTAINER

This is a continuation of copending application(s) Ser. No. 07/387,347 filed on July 28, 1989, now abandoned.

BACKGROUND OF THE INVENTION

The present invention relates in general to disposable containers employed in hospitals for disposing of medical wastes and more specifically to such a container suitable for use in the patient's room in a hospital into which medical instruments and materials employed in treating the patient in the patient's room can be safely stored prior to disposal and subsequently disposed of in a secure and economical manner.

Various types of containers have been developed heretofore for receiving medical wastes in hospital surgery and treatment rooms which are intended to protect the doctor, nurse or other hospital personnel from injuring themselves during the disposal procedure. It is very important that used medical instruments, such as surgical sharps, needles and syringes, or the like, be disposed of in a hospital environment in such a way that no one receives a scratch or puncture and the attendant exposure to contamination. Examples of disposable containers for use in surgical room environments are disclosed in prior Pat. Nos. 4,494,652 entitled "Container For Sharps"; 4,552,280 entitled "Container For Waste Products; 4,453,648 entitled "Disposal Bin"; 4,580,688 entitled "Container Having Plural Closures"; and Pat. application Ser. No. 838,296 filed Mar. 10, 1986 entitled "Rigid Disposable Container For Holding and Dispensing of Used Medical Sharps and Other Medical-Surgical Materials."

Currently, it is still common practice to dispose of medical materials in a patent's room by simply depositing the same in a standard type of wastebasket or the materials or instruments are removed and disposed of at some distant location. It is desirable to have a disposable container which by its appearance, construction and mode of operation can be utilized in the environment of a patient's room so that the doctor, nurse or other hospital personnel treating a patient in the patient's room can quickly and simply dispose of the medical instrument, sharp or other medical material in a safe and secure manner into a container which stores the same until such time as the container is sufficiently filed, or the patient is released from the hospital, so that the container can then be securely sealed and disposed of. Examples of commercially available disposable containers used in hospital patient rooms heretofore are the "SHARPS-A-GATOR" (a trademark of Devon Industries, Inc., Chatsworth, CA) sharp collection and disposal system and the "Roll-A-Way" (a trademark of Premium Plastics, Inc., Chicago, Ill.) sharps disposal system. These products have dual closure features including a top, lockable closure flap, which is closed completely only once just before disposal, and additional barrier means below the flap which are intended to allow entry of medical instruments and waste while keeping the patients, doctors or nurses from entering the container body. These additional barriers have comprised bendable flaps which cover a portion of the container inlet, rotating paddle wheels and normally closed pivoted flappers gravity biased to a normally closed position.

It would be desirable to provide such disposable containers with stationary barrier means which do not have to bend, pivot or rotate to allow entry of the disposed medical instrument and/or waste but still prevent manual entry into the container body. Further, it would be desirable to have such a container where the contained instruments and/or waste will not fall out if the container is inverted prior to closure of the locking closure flap. It would also be desirable to have such a container where a closure arrangement of a given size could be easily adoptable to fit upon container bodies of differing size to accommodate different volumes of stored medical instruments and/or waste for subsequent disposal thereof.

SUMMARY OF THE INVENTION

In view of the foregoing, it is a primary object of the present invention to disclose and provide a disposable container for use in a hospital patient's room which allows for the safe disposal of medical instruments, such as syringes or the like, while preventing the user's fingers from entering into a storage area within the container so as to prevent accidental engagement between the user's fingers and the contents of the containers. It is further an object of the present invention to disclose such a container wherein the disposed of medical instruments are positively retained within the container, prior to closing the lockable closure lid, even if the container is inverted. It is a further object of the present invention to provide such a container which is economical to manufacture, easy to store in preparation for use and which is simply and easily assembled into a usable form ready to be used in a hospital patient's room in a safe and generally error proof manner.

It is still another object of the present invention to provide such a container which is easily adaptable to provide different size storage capacities.

Generally stated, the medical instruments disposal container in accordance with the present invention comprises the provision of a hollow base or bin having a top flange and a hollow top housing having a footing flange, the base top flange and housing footing flange having being provided to snap fit together through mating snap lock tabs and apertures. A generally rectangular entry port is provided in an upper portion of the top housing to provide for entry of disposable materials into the container. A closure lid is provided adjacent the entry port for closing the port prior to disposal in a substantially permanent manner to facilitate the entrapment of disposed materials within the container during the disposal process. As particularly contemplated within the present invention, normally stationary tortuous path means are provided in the hollow top housing below the entry port to provide a tortuous entry passage into the container cavity from the entry port which allows for the unrestricted passage of medical instruments and/or waste past stationary surfaces while preventing manual entry to the container interior.

More specifically, the present invention in medical instruments disposal container comprises the provision of a container with an instrument receiving and disposal passage which is provided with a first barrier wall disposed within the top housing which spans the interior thereof in a first direction, is inclined relative the vertical extent of the housing and spans approximately one half of the extent of the housing which underlies the entry port in a second direction which is perpendicular to said first direction and a second barrier wall disposed within the housing and below said first barrier wall, such second barrier wall spanning the interior of the housing in said first direction, being inclined relative the vertical extent of the housing and facing opposite of the first barrier wall and spanning approximately one half of the extent of the housing which underlies the entry port in the second direction, whereby the passage through the top housing is provided at least in part by a space provided between such barrier walls.

In a preferred embodiment, mounting means are provided for normally positioning one of the inclined barrier walls in a stationary position during normal medical waste disposal operations but which pivots to close against the other barrier wall of said walls when inverted whereby upon inversion of the container such one of the barrier walls moves by the force of gravity acting thereon to close the medical discards passage formed between the barrier walls. Such mounting means may be associated with the lower one of the two barrier walls and preferably includes pivot means for pivotally mounting such one of the two barrier walls along an upper longitudinal portion thereof. A gravity responsive mass may be provided in association with such one of the two barrier walls generally below the pivot means whereby said one of the walls pivots in a predetermined manner to close the passage on inversion of the container.

An alternative embodiment, of the disposable container is provided in three easily assembled parts wherein a first part includes an opened top bin suitable for receiving and storing medical instrument discards and provides a storage capacity of selectable size, a second member being an adaptor member having an open top and bottom portions of different size the bottom portion being adapted to fit on the top of the selected size bin and the open top portion meeting with the bottom of a top member, such top member being the third part of the assembly and containing both the manually lockable closure lid and the tortuous path means discussed hereinbefore within the top member. Snap fit interlocking means are provided between the three parts to provide for their easily assembled interfitted relationship wherein the adaptor member facilitates use of a given size top member with a larger capacity bin via the interengagement provided by the adaptor member.

A more complete understanding of the present invention in a medical instrument disposal container, as well as a realization of additional advantages and objects therefor, will be afforded to those skilled in the art from a consideration of the following detailed description of the a preferred exemplary embodiment two modification thereof. Reference will be made to the appended sheets of drawings which will be first briefly described.

BRIEF DESCRIPTION OF THE DRAWINGS

FIG. 3 is a detail section view of a top housing portion of the container of FIG. 2 taken therein along the plane III—III.

FIG. 4 is a detail view of a portion of the container as seen in FIG. 3 taken therein along the plane IV—IV.

FIG. 5 is a detail view of the upper portions of the container as seen in FIG. 3 with the closure lid shown in a closed, snap lock position for disposal of the container.

FIG. 11 is a perspective view from above the front and right hand sides of an alternative exemplary embodiment of the disposable container in accordance with the present invention showing a three-part easily assembled arrangement wherein the top member, including a manually lockable closure lid and internal tortuous path means, is fitted by an intermediate adaptor member to a larger capacity bin than the bin illustrated in association with the embodiments of FIGS. 1 through 10.

FIG. 12 is a section view through the container of FIG. 11 taken therein along the plane XII—XII.

FIG. 13 is a detail section view taken along the plane XIII—XIII in FIG. 11.

DETAILED DESCRIPTION OF THE EXEMPLARY EMBODIMENTS

Figure 2:
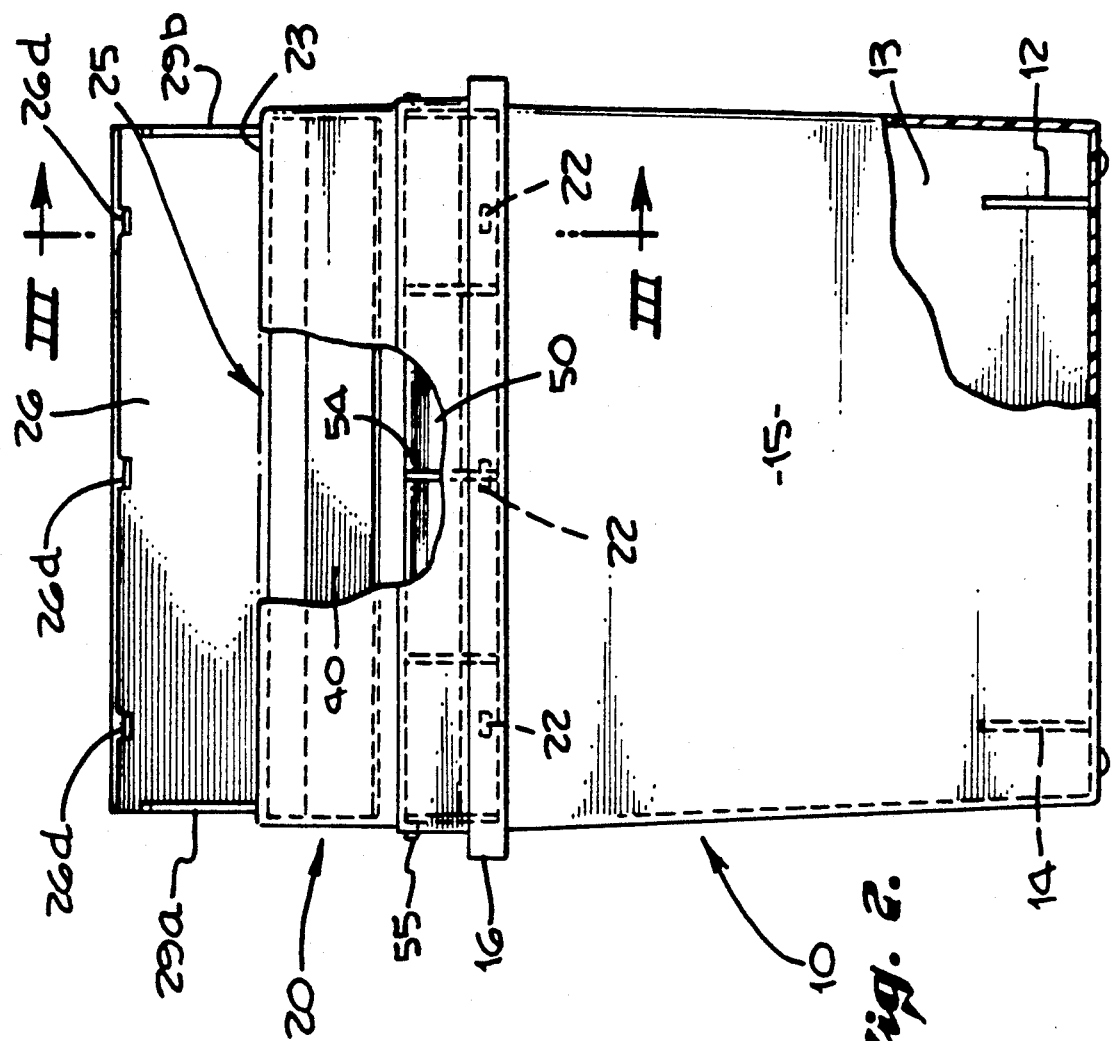
FIG. 2 is a front elevational view, partially in section, of the container of FIG. 1 when viewed from the plane II—II thereof.
Figure 1:
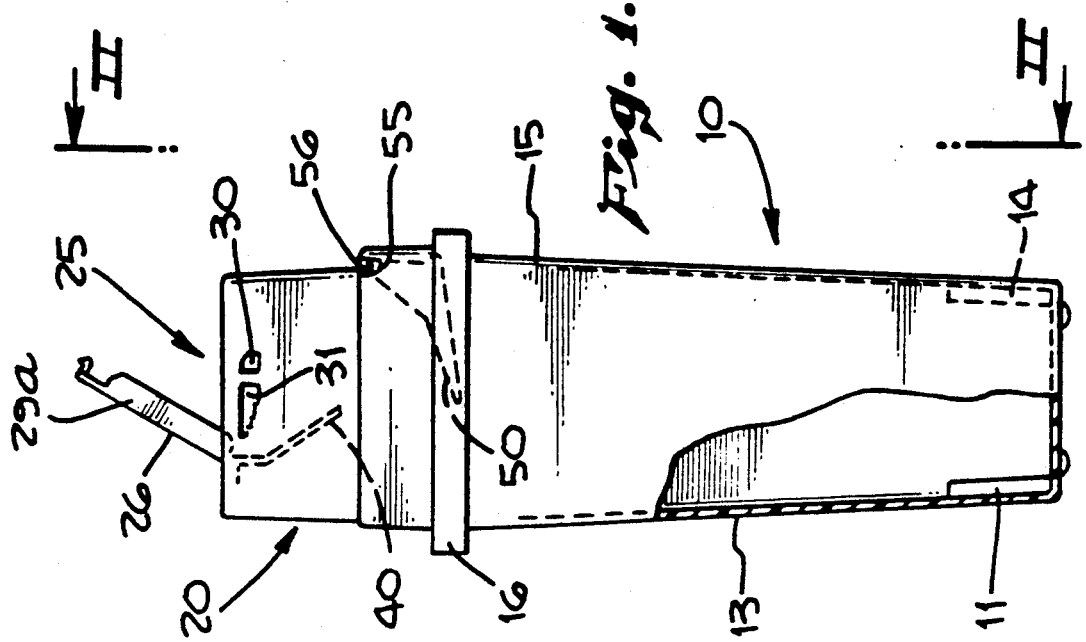
FIG. 1 is a side elevational view, partially in section, of a preferred exemplary embodiment of medical instruments disposal container for use in a hospital patient's room for storage of used medical syringes and the like in the patient's room prior to closure and subsequent disposal thereof in accordance with the present invention.

Referring initially to FIGS. 1 through 8, a preferred exemplary embodiment of the medical instruments disposal container, in accordance with the present invention, is provided for the reception and storage of used medical materials including surgical sharps, syringes, and the like, which may be used by doctors and hospital personnel during the treating of a patient in the patient's room. Such instruments and materials may be stored within the hollow base member indicated generally at 10 maintained within the patient's room prior to subsequent disposal of the container and its contents. Base member or bin 10 is preferably made of a light weight plastic material with upwardly divergent side walls as seen in FIGS. 1 and 2 to facilitate the stacking of the base members prior to their being placed in use. In order to facilitate the separation of such stacked bins, each of the bins has a pair of stop flanges on the front and back walls, as flanges 11 and 12 on back wall 13, and stop flange 14 on front wall 15. A second stop flange on front wall 15 across from back wall stop 12 is not seen in the drawings.

The hollow base member or bin 10 is provided with a hollow top member or housing, indicated generally at 20, which is seated upon and snap locked to bin 10. As best seen in FIGS. 1 and 3, the bin 10 has a support flange 16 molded integrally of the upwardly facing open end thereof, the flange 16 being provided with a plurality of snap locking tab receiving aperture, such as apertures 17 as seen in FIG. 3. Such apertures are formed in a horizontal seating flange portion 18 which is integral with the surrounding peripheral flange 19 which extends above and below the seating flange portion 18.

The hollow top housing, indicated generally 20, is provided with footing flange 21 extending about the downwardly facing open end and is configured, as seen in FIGS. 3 and 4, to seat upon the support flange 16 along the upper surface of the seating flange portion 18. A plurality of snap lock tabs, as tabs 22 as seen in FIG. 3, are formed integrally of the top housing footing flange 21 to depend therefrom in order to snap lock into the tab receiving apertures, as aperture 17 in FIG. 3, to effect a locking assembly of the hollow top housing 20 to the hollow bottom bin 10 by simply assembling and pressing the two members together. By configuring the tabs, as tabs 22, to be somewhat wider than the width of the apertures, the snap assembly thereof tends to provide a substantially permanent assembly of the top housing onto the bottom bin.

Medical instruments and materials may be placed through the top housing 20 via the entry port, indicated generally at 25, provided in the top housing as best seen in FIG. 3. Such entry port, in the exemplary embodiment, is provided in the top surface 23, as seen in FIG. 3, with a portion of the top surface being provided by a recessed flange 23a extending about upper portions of the top housing. A closure lid 26 is assembled to the top surface 23 to close over the entry port just prior to disposal of the container. Lid flange 26a has snap lock type fasteners 26b by which the lid is attached to the housing 20, the lid being moveable mounted by the an integral, living hinge, construction, indicated generally at 27, the provision of which is per se known in the art. As is seen from a comparison of FIGS. 3 and 5, the closure lid 26 is provided for closing the entry port, indicated generally 25, to facilitate disposal of the container with the contents securely sealed therein. In order to maintain the closure lid in its closed, disposal condition, the outer edge 26c of the lid is provided with a plurality of spaced, depending snap tabs 26d which are adapted to be press fit through, and lock relative to, a mating plurality of lid tab receiving apertures 28 provided in the upper surface flange 23a.

Needle remover means are provided in the container of the present invention to facilitate the easy removal of needles from vacuum type syringes in a safe and secured manner. Such means in the exemplary embodiment includes the provision of the apertures 30 and 31, configured as best seen in FIGS. 1 and 3, to facilitate the introduction of the needle into the hollow top housing and the convenient removal thereof from an associated vacuum syringe without the need for handling the needle The used syringe may then be dropped through the entry port 25, with lid 26 in its open position, to be received and guided by the tortuous path means, indicated generally at 40. Closure flanges 29a and 29b are provided on lid 26, as seen in FIGS. 1-3, flange 29b closing the apertures 30 and 31 when lid 26 is closed as seen in FIG. 5.

As is particularly contemplated within the present invention, tortuous path means are positioned within top housing 20 below the rectangular entry port, indicated generally at 25, to normally block manual entry to the interior of hollow base member or bin 10, so that the doctor, hospital personnel or patient cannot place their fingers into the interior of the container to be contaminated, cut or otherwise injured by the contents of the disposal container.

In the exemplary embodiment of FIGS. 1 through 7, such tortuous path means comprise the provision of a first barrier wall 40 and a second barrier wall 50 within the top housing 20 such that medical instruments, discards or waste dropped into the top housing through the entry port 25 will fall through a direction changing, tortuous passage provided by the surfaces of walls 40 and 50 to the interior of bin 10 while, at the same time, inadvertent manual entry by the user into the interior of bin 10 is prevented. First barrier wall 40, as best seen in FIGS. 1 through 3, is disposed within upper portions of top housing 20, being formed integrally thereof in the exemplary embodiment, to span the interior of the housing in the side to side direction as seen in FIG. 2. A plurality of webs, as web 42 as seen in FIG. 3, are provided integrally of wall 40 to give the wall support in its position below entry port 25, the wall 40 being inclined relative the vertical extent of top housing 2, as seen in FIG. 3, toward the front portion o the container. As best seen in FIG. 3, the forward direction of extent of the downwardly, bu forwardly inclined wall 40 is such that its spans approximately one-half of the extent of said housing which directly underlies the inlet port, indicated generally at 25, in the front to back direction of the container. This first barrier wal40 prevents the user from putting their hand easily into the bin since the hand would normally be inserted form the front of the container under the open lid 26 and abut the forwardly facing barrier wall 4. Any medical instruments, discards or waste deposited int the same manner would tend to impinge upon the forward facing wall of barrier 40 and be directed by gravity downwardly toward the forward interior portion of top housing 20.

Figure 6:
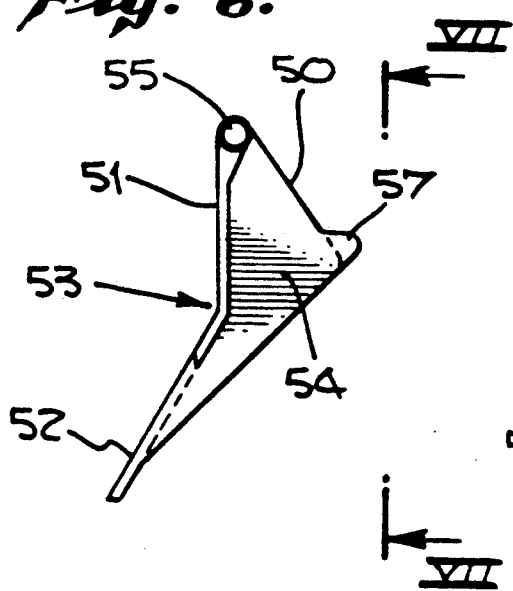
FIG. 6 is a side view of the exemplary embodiment of tortuous path second barrier wall employed in the exemplary container of FIGS. 1 through 5.
Figure 7:
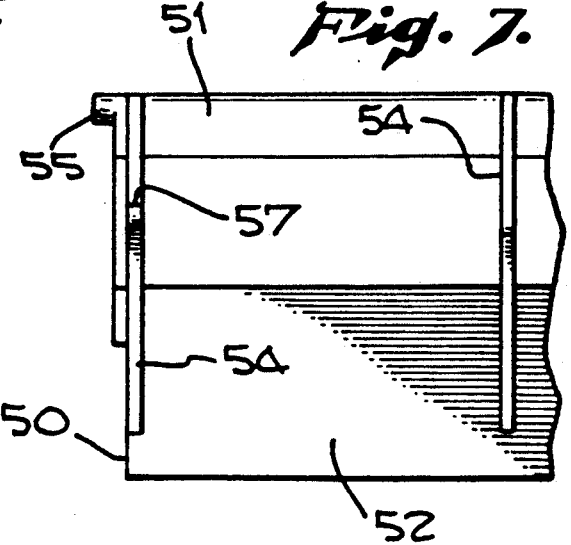
FIG. 7 is a plan view of the second barrier wall of FIG. 6.

The second barrier wall 50 is also disposed within housing 20k but in a lower portion 20a thereof below he first barrier wall 40 as seen in FIGS. 1 through 3. Second barrier wall 50 is provided to span the interior of housing 20 in the side to side, lateral direction in the same manner as does wall 40. Barrier wall 50 is inclined relative the vertical extent of housing 20 in a downwardly and rearwardly inclined direction opposite to that of the downward forwardly facing inclination of wall 40. As best sen in FIG. 3, the lower, second barrier wall 50 has an upper fairly steeply inclined portion 51 and a lower, less steeply inclined portion 52 providing a valley or wall portion puncture indicated generally at 53. Medical instruments, discards or waste falling from inlet 25 would normally first contact, engage and roll down wall 40 in a forward falling direction to impinge upon the lower second barrier wall 50 generally in the area of the wall portion junction indicated generally at 53. Since both barrier walls 40 and 50 are stationary in the above described functioning of the container when it is in its upright position, the medical instruments, discards or waste simply fall through the tortuous path, without any internal moving parts of the container having to be manipulated or respond to the weight of the instrument, discard or waste as the same fall by gravity into the interior 10a of bin 10. The provision of both normally stationary walls 40 and 50 also provides a tortuous passage which normally prevents manual entry into the interior of bin 10 so as to avoid inadvertent contact between the container user's hands or fingers with any of the dispose items within h bin. As seen in FIGS. 6 and 7, in the present exemplary embodiment, second barrier wall 5 is a molded element having the aforementioned lateral extent with structural flanges, as flanges 54 spaced along a rear surface thereof.

Figure 8:
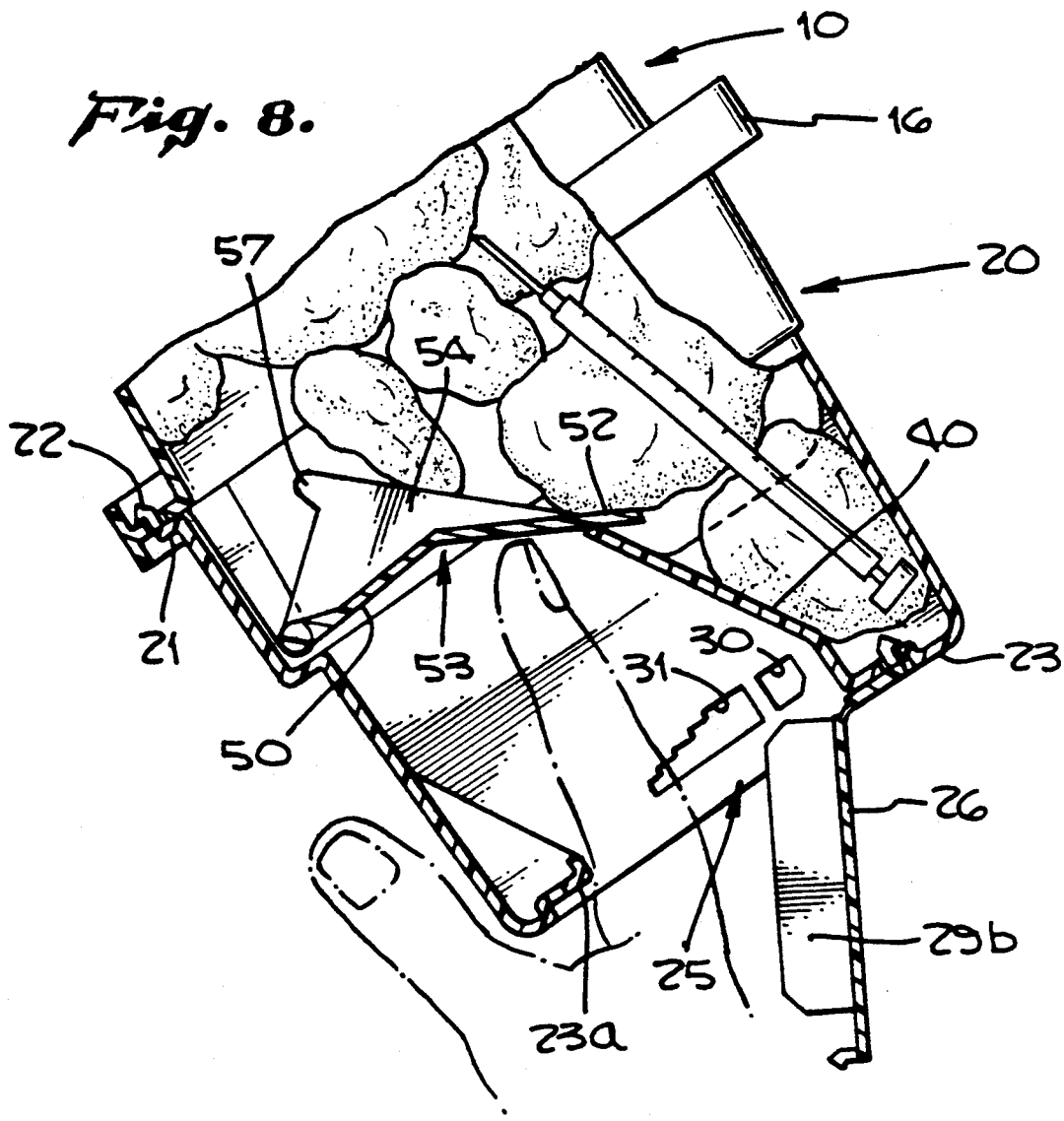
FIG. 8 is a side view, in section, of the exemplary embodiment of disposal container of FIGS. 1 through 7 shown in an inverted position with the lower barrier wall having fallen by gravity against the upper barrier to close off the interior of the container.

In the exemplary embodiment of FIGS. 1 through 7, mounting means are provided for normally position in the lower, second barrier mean 50 in a stationary position during normal medical instrument and/or waste disposal. operation, but which pivots to close against the upper barrier wall 50 when inverted so that upon inversion of the container, barrier wall 50 pivots by gravity, and the weight of any disposed items within the bin so as to close the internal opening, indicated generally 60 in FIG. 3, such closure of the internal opening being illustrated in FIG. 8. Such mounting means in the exemplary embodiment includes the provision of laterally protruding end post or journal pins, as pin 55 in FIGS. 6 and 7, on either end of the barrier wall 50. Suitable mounting apertures, as aperture 56 as seen in FIGS. 1 and 4, may be provided at opposite ends of the lower portion 20a of housing 20 in order to pivotally mount the second barrier wall 50 to pivot about its upper edge as seen in FIGS. 3 and 8 only when the disposable container is inverted, as seen in FIG. 8, the barrier 50 normally being stationary with its positioning tabs 57 abutting the adjacent interior wall of top housing lower portion 2a. With reference to FIG. 8, the medical instruments, discards and waste contained within bin 20 will fall on the underside of the barrier wall 50 in accordance with the invention of the present embodiment in disposable container, whereby the same will not inadvertently fall out of the container and, as illustrated in FIG. 8, the manual contact between the user's fingers and the inverted contents of the container is prevented.

Figure 9:
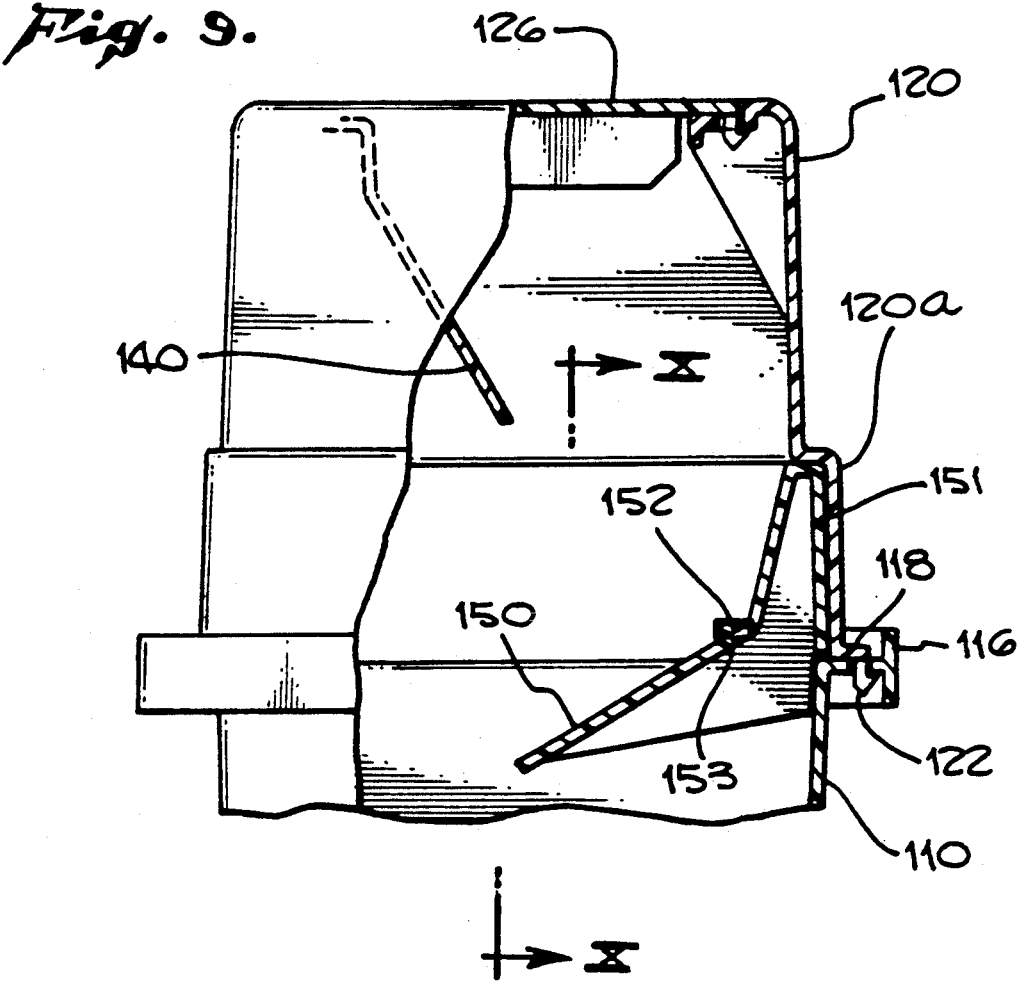
FIG. 9 is a view as in FIG. 3 showing an alternative embodiment of second barrier wall of the tortuous path below the container inlet port.
Figure 10:
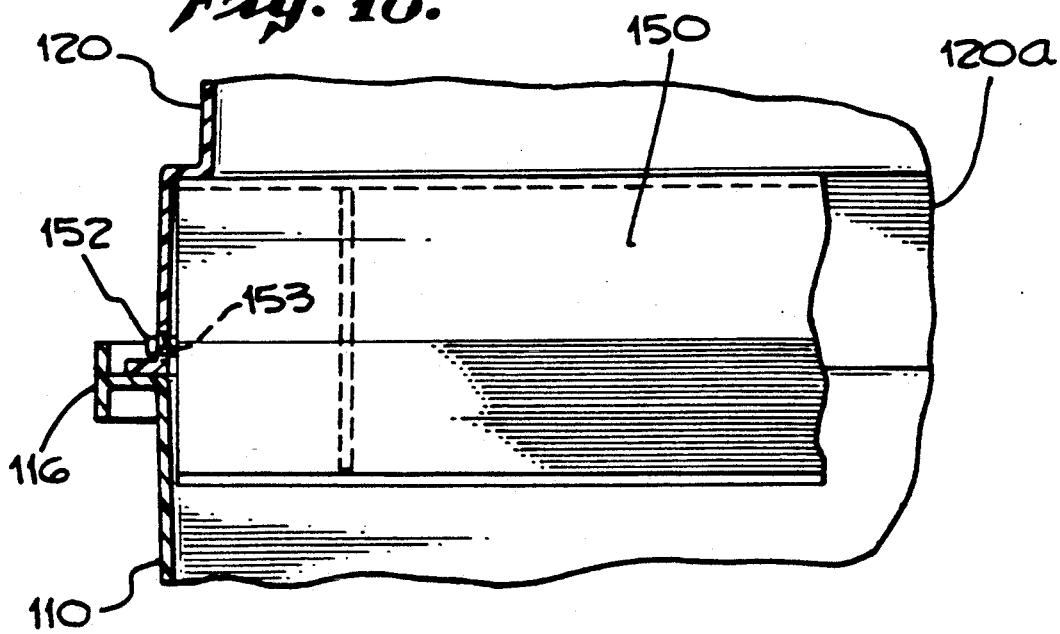
FIG. 10 is a detail view of the second barrier wall of FIG. 9 taken therein along the plane X—X.

An alternative exemplary embodiment is illustrated in FIGS. 9 and 10 wherein both the barrier walls 140 and 150 are stationary at all times. In this alternative embodiment, the exemplary top housing 120 is mounted to the lower base or bin 110 in the same manner as before wherein a plurality of depending tabs 122 are adapted to snap through openings 118 in the flange 116 of bin 110. Closure flap 126 and first barrier wall 140 are provided in the same manner as these elements where described in association with the prior embodiment. However, the second barrier wall 150 in this embodiment is not provided to pivot or move at any time.

As seen in FIGS. 9 and 10, the lower, stationary second barrier wall 150 has a rear wall 151 which is secured to an inner surface of lower portion 120a of top housing 120 and has laterally protruding locating pins as pin 152, on opposite ends thereof which fit into locating apertures, as aperture 153 in opposite side walls of the housing lower portion 12a. Barrier walls 140 and 150, as described hereinbefore, as with regard to the prior embodiment, provide a barrier to manual entry into the interior of bin 110 by the user's hands or fingers while providing a reliable, no moving part, tortuous path entry for any medical instruments, discards or waste being deposited into bin 110 via the inlet port, which is shown closed in the illustration of FIG. 9 by the closure lid 126.

The passage of the medical instrument through the tortuous path barrier walls will align the instrument parallel to the barrier walls which assures neat and orderly alignment in the container. This alignment feature allows more instruments to be accumulated.

Referring now to FIGS. 11 through 13, a further alternative embodiment of disposable container, in accordance with the present invention, is disclosed wherein the container is provided in a three part easily assembled arrangement wherein the hollow top housing, indicated generally at 220, is provided in the same manner as in the prior embodiments and is fitted to a larger size bin or base member 210 by means of an adaptor member indicated generally at 260. As seen in FIG. 12, the hollow top housing, indicated generally at 220, is provided with a footing flange 221 extending about the downwardly facing open end of the housing and is provided with a plurality of tabs 222 as in the prior embodiments. The lower end of first barrier wall 240 and the entirety of the second, lower barrier wall 250 may be seen as comprising the tortuous path means, as in the prior embodiments, in the top housing of the present embodiment.

Bin 210 is provided in the form of a larger capacity bin than that illustrated in the embodiments of FIGS. 1 through 10 and is provided with a support flange 216 which in the present embodiment has a surrounding peripheral flange 217 which depends from the support flange 216.

The adaptor member, indicated generally at 260 in the exemplary embodiment includes a plurality of tab receiving pockets 261 located inwardly of a top annular rib 262 to receive the top housing footing flange 221 within the rib and the tabs 222 snapped into the pockets 261 as seen in FIG. 12. In order to facilitate the fit of the adaptor member to the larger size bin 210, the adaptor member is provided with locking tabs 263 on the peripheral flange 264, as seen in FIG. 12, to snap under the depending peripheral flange 217 of the bin. Such snap fit is enhanced by the provision of retainer webs 265 on the interior of the adaptor member which wedge the tabs 263 tightly under the bin flange 217 through the engagement of inner surfaces of bin wall 266 by the retainer end cam portions 267. A handle portion 268 may be molded into one end of the adaptor member to facilitate manipulation of the container, particularly when the container has been filled, the closure lid 226 has been closed and it is desired to dispose of the container and its contents.

Having thus described exemplary embodiments of the medical instrument disposal container in accordance with the present invention, it should now be apparent to those skilled in the art that the various objects and advantages afford stated have been obtained. The container of the within invention provides for easy access, through a rectangular entry port for the introduction of medical sharps, syringes and other medical materials while preventing the patients, doctors or medical personnel's fingers from entering the storage portion of the container bin beneath the barrier members. The lower barrier member of the preferred embodiment is provided to normally remain stationary during introduction of syringes, discards and medical materials into the storage portion of the container preventing accidental needle stick injuries even as the bin fills. If the container in inverted, the preferred embodiment of second barrier wall pivots to close the passage between to prevent accidental discharge of the bin contents.

It should also be appreciated by those skilled in the art that various modifications, adaptations and alternative embodiments may be made within the invention in medical instruments disposal container disclosed herein which is defined by the following claims.

What is claimed:

1. In an in-patient room medical discards receiving, storage and disposal container which is portable and manually invertible and has an open to storage bin, a hollow top housing having a discards inlet having a lateral extent relative said container and an open bottom with a mechanical snap lock type closure lid to overlie said inlet and means for connecting said top housing to said storage bin in an effectively permanent assembly with said inlet communicating with the interior of said bin through said housing the improvement comprising the provision of:

tortuous path means in said housing for providing a passage through said housing suitable for medical discards to fall from said inlet though a direction changing passage o the interior of said bin while preventing manual entry to said interior so as to prevent inadvertent contact between the hands of the container user and medical discards within said bin, wherein said tortuous path means comprises:

a first normally stationary barrier wall disposed within said housing and spanning the interior of said housing below said inlet in a first direction which is generally parallel to he lateral extent of said inlet, being inclined relative the vertical extent of said housing and spanning approximately one half of the extent of said housing which underlies said inlet in a second direction which is generally perpendicular to said inlet lateral extent;

a second normally stationary barrier wall disposed within said housing and below said first barrier wall, said second barrier wall spanning the interior of said housing in said first direction, being inclined relative the vertical extent of said housing and facing opposite of said first barrier wall and spanning approximately one half of the extent of said housing which underlies said inlet in said second direction whereby said direction changing passage through said housing is provided by upper surfaces of said barrier walls to provide for straightening of instruments deposited in said inlet for parallel alignment in the container bin; and wherein:

mounting means are provided or normally positioning one of said inclined barrier walls in a stationary position during normal disposal operations with said container in an upright position and for movement when inverted whereby upon manual inversion of said container said one of said barrier walls moves by the force of gravity acting thereon to close said passage.

2. The improvement in container of claim 1 wherein: said mounting means is associated with the lower one of said two barrier walls and includes pivot means for pivotally mounting said one of said two barrier walls along an upper longitudinal portion thereof.

3. The improvement in container of claim 2 wherein: the center of gravity of said one of said two barrier walls lies below said photo means whereby said one of said walls pivots toward said entry port in a predetermined manner when inverted to abut against the other of said walls and thereby close said passage on inversion of said container.

4. A portable and manually invertible medical discards container having a top inlet positioned above a storage space within said container, and a tortuous path means between said inlet and said space whereby medical discards deposited into said storage space via said inlet pass through a tortuous passageway, said tortuous path means comprising:

a first normally stationary barrier element including a rear mounting wall engaging an inner wall of said container and a first barrier walla inclined downwardly from said inlet and facing in a given direction;

a second barrier element including a second barrier wall inclined downwardly from said inlet and mounting means for mounting said second barrier wall to be normally stationary in use when said container is upright and which is generally opposite of and facing toward, but below, said first barrier wall relative said inlet whereby;

medical discards released into said inlet initially engage and slide down said first barrier wall in a first direction and then drop onto said second barrier element and slide down said second barrier wall in a second direction into said storage space; and wherein said means for mounting said second barrier wall includes pivot means connected between said second barrier wall and a second inner wall of said container so as to cause said second barrier wall to fall by the force of gravity acting thereon into passageway closing relation to said first barrier wall when said container is turned upside down whereby medical discards within said storage space are retained therein against inadvertent release from said container when it is manually turned upside down.

5. The medical discards container of claim 4 wherein: said first barrier element and second barrier element are both provided within a top portion of said container which is separately provided as an assembly component; and an adapter portion is separately provided with means for snap locking to said top potion and to a bin portion of said container whereby said top portion may be adapted to fit different size bin portions.

6. A potable and manually invertible medical discards container having a top inlet positioned above a storage space within the container and tortuous path means within said container cooperating with said inlet whereby medical discards deposited into said storage space vis said inlet pass through a tortuous passageway, said tortuous path means comprising:

a first barrier element including a first barrier wall inclined downwardly relative said inlet and facing in a given direction;

a second barrier element including a second barrier wall inclined downwardly relative sad inlet;

mounting means for mounting said second barrier wall generally opposite of sand below said firs barrier wall relative said inlet, said mounting means including pivot means connected between said second barrier wall and an interior portion of said container whereby;

medical discards released into said inlet initially engage and slide down said first barrier wall in a first direction and then drop onto said second barrier element and slide down said second barrier wall in a second direction into said storage space and, in he event that said container is manually turned upside down said second barrier wall will fall by the force o gravity acting thereon into passageway closing relation to said first barrier wall whereby medical discards within said storage space are retained therein against inadvertent release from said container when it is upside down.

7. A potable and manually invertible medical discards container having a top inlet positioned above a storage area within the container and tortuous path means within said container cooperating with said inlet whereby medical discards deposited into said storage area via said inlet pass through a tortuous passageway, said tortuous path means comprising:

a first normally stationary barrier wall inclined downwardly relative said inlet and facing in a given direction and having a lower end;

a second barrier wall inclined downwardly relative said inlet and mounting means or mounting said second barrier wall to be normally stationary in use when said container is upright and to pivot said second barrier wall into a position closing said passageway upon inversion of said container, said second barrier wall normally positioned generally opposite f and facing toward but below, said fist barrier wall relative said inlet to provide a space therebetween for discards to pass between said first and second barrier walls whereby;

medical discards released into said inlet must initially engage and slide down said first stationary barrier wall in a first direction, then drop through said space onto said second barrier wall and then slide down said second barrier wall in a second direction into said storage area.

8. In an in-patient room medical discarded instruments receiving, storage and disposal container which is portable and manually invertible and has an open top storage bin, a hollow top housing having a discards inlet and an open bottom and means or connecting said top housing to said storage bin with said inlet communicating with the interior of said bin through said housing the improvement comprising the provision of:

tortuous path means for providing a direction changing passage through said housing suitable for said medical instruments to fall from said inlet though said direction changing passage through said housing o the interior of said bin while preventing manual entry to said interior so as to prevent inadvertent contact between the hands of the container user and medical discards within said bin, said tortuous path means including:

a first normally stationary barrier wall having a lower end and being inclined relative the vertical extent of said container, said first stationary barrier wall underlying said inlet to deflect discards received through said inlet in a first direction;

a second normally stationary barrier wall disposed below said first barrier wall, spaced from said lower end to provide a space therebetween, being inclined relative the vertical extent of said container and facing opposite of said first barrier wall whereby said direction changing passage through said housing is provided by upper surfaces of said barrier walls and said space therebetween to provide for straightening of instruments deposited in said inlet into generally parallel alignment in the said bin; and wherein:

mounting means are provided for normally positioning said second barrier wall in a stationary position during normal disposal operations with said container in an upright position and for allowing movement of said second barrier wall when inverted whereby upon manual inversion of said container said second barrier wall moves by the force of gravity acting thereon to close said space between said walls and thereby close said passage.

9. A medical instrument disposal container which is portable and manually invertible and has a hollow base, a hollow top housing and means for assembling said housing to said base, said housing having a generally rectangular entry port to receive discarded syringes and comprising:

normally stationary tortuous path means to provide a tortuous entry passage into said base from said port which allows for the unrestricted passage f instruments including syringes past normally stationary surfaces while preventing manual entry to the interior of said base, said path means further including a first normally stationary barrier wall providing a first surface inclined downwardly relative the vertical extent of said container and positioned to receive instruments passed through said port to cause them to move in a first downward direction toward said interior of said base, an open space at an end of said first surface through which said instrument fall after they have moved downwardly along said first surface and a second normally stationary barrier wall providing a second surface inclined downwardly relative the vertical extent of said container, facing oppositely of said first surface and positioned below said space to receive instruments falling through said space and to direct them in a generally opposite direction relative the direction of movement of said instruments on said first surface for storage in said base; and wherein:

mounting means are provided for normally positioning said second barrier wall in a station position during normal upright use of said container and for movement to a passage closing position when said container is manually inverted.

10. The medical instruments disposal container of claim 9 wherein:

said mounting means positions said second barrier wall to close said space through engagement with said first barrier wall when said container is inverted to thereby close said passage.

* * * * *